(12) United States Patent
Fujita et al.

(10) Patent No.: US 6,180,844 B1
(45) Date of Patent: Jan. 30, 2001

(54) COMPOSITION CONTAINING FLUORESCENCE-GENERATING SUBSTRATE

(75) Inventors: Satoshi Fujita, Aichi-ken; Naoto Kagiyama, Tokyo; Yasumitsu Kondoh, Hokkaido; Paidi Yella Reddy; Takeshi Toru, both of Aichi-ken, all of (JP)

(73) Assignee: Aisin Seiki Kabushiki Kaisha, Kariya (JP)

( * ) Notice: Under 35 U.S.C. 154(b), the term of this patent shall be extended for 0 days.

(21) Appl. No.: 09/264,678

(22) Filed: Mar. 9, 1999

(30) Foreign Application Priority Data

Mar. 9, 1998 (JP) .................................................. 10-073094
Dec. 28, 1998 (JP) .................................................. 10-376986

(51) Int. Cl.[7] .................................................. C07C 13/00

(52) U.S. Cl. .................................. 585/24; 585/25; 585/26; 435/5; 435/6; 536/23.1; 536/25.3; 536/25.32

(58) Field of Search .................................. 536/25.3, 23.1, 536/25.32; 435/5, 6; 585/24, 25, 26

(56) References Cited

PUBLICATIONS

Shiga et al. "A novel method for determining peroxidaes activities using p–acetamidophenol analogs" Analytical Sciences, vol. 11, pp. 195–201, Apr. 1995.*
Alvaro Sanchez Ferrer et al, "Fluorescence Detection of Enzymatically Formed Hydrogen Peroxide in Aqueous Solution and in Reversed Micelles", Analytical, Biochemistry 187, 129–132 (1990).

*Primary Examiner*—Jezia Riley
(74) *Attorney, Agent, or Firm*—Oblon, Spivak, McClelland, Maier & Neustadt, P.C.

(57) ABSTRACT

A fluorescent dye-forming composition is provided that contains a fluorescence-generating substrate of formula (I):

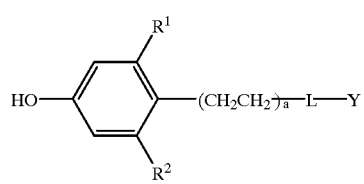

(I)

where $R^1$ and $R^2$ are each independently a hydrogen atom, or an electron-donating group selected from a lower alkyl group, a lower alkoxy group, a hydroxyl group, an alkylcarbonyloxy group, an amino group di-substituted with a lower alkyl group, and an aryl group;

L is selected from —NHCO— or —CONH—;

Y is selected from -alkylene-COOH or formula (II):

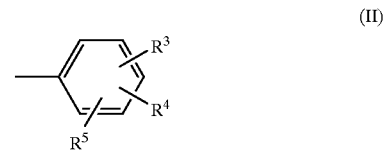

(II)

where $R^3$, $R^4$ and $R^5$ each independently represent a hydrogen atom, carboxyl group, or an electron-donating group selected from a lower alkyl group, a lower alkoxy group, a hydroxyl group, an alkylcarbonyloxy group, an amino group di-substituted with a lower alkyl group, and an aryl group. Alternatively, two of $R^3$, $R^4$ and $R^5$ form, together with the adjacent carbon atoms to which they bond, a fused 5-membered or 6-membered hydrocarbon ring. Alkylene represents a linear or branched $C_{1-6}$ alkylene group; and a represents an integer of 0 or 1. The substrate forms a fluorescent dye having good binding to biological samples.

22 Claims, 1 Drawing Sheet

OTHER PUBLICATIONS

Kiyoshi Zaitsu et al, "New Fluorogenic Substrates for Horseradish Peroxidase: Rapid and Sensitive Assays for Hydrogen Peroxide and the Peroxidase", Analytical Biochemistry 109, 109–113 (1990).

P. David Josephy et al, "Co–Oxidation of Benzidine by Prostaglandin Synthase and Comparison with the Action of Horseradish Peroxidase," The Journal of Biological Chemistry, vol. 258, No. 9, Issue of May 10, pp. 5561–5569 (1983).

Satoshi Fujita et al, "A Novel Fluorogenic Substrate for Horseradish Peroxidase: Efficient Detection of Membrane–Bound Nucleic Acids and Simultaneous Detection of DNAs", The Chemical Society of Japan, Chemistry Letters pp. 1075–1076 (1997).

Edward Sheldon et al, "Nonisotopic M13 Probes for Detecting the Beta–Globin Gene: Application To Diagnosis of Sickle Cell Anemia", Clin. Chem. 33/8, 1368–1371 (1987).

Derwent Abstract, "Method for Determining Peroxidase and Substance Having Catalyst Equal to That of the Same" Accession No. 95–039393, 1995.

Derwent Abstract, "Quantitative Measurement of Peroxidase and Equiv. Catalysing Substance—Using P–Hydroxy Acetanilide Based Fluorescence Reagent in Presence of Hydrogen Peroxide, Peroxidase and Catalysing Substance" Accession No. 95–117868/16, 1995.

* cited by examiner

COMPOSITION CONTAINING FLUORESCENCE-GENERATING SUBSTRATE

BACKGROUND OF THE INVENTION

Field of the Invention

The present invention relates to a composition containing a fluorescence-generating substrate or fluorescent dye precursor. More specifically, it relates to a composition and methods useful in detecting biological analytes.

BACKGROUND OF THE INVENTION

Heretofore, radioactive isotopes, coloring substrates, as well as fluorescent dyes and their precursors (or fluorescence generating substrates) have been widely used to detect biological analytes. In particular, fluorescence-generating substrates are now widely used and studied for enzyme-linked immunosorbent assays, in which an alkali phosphatase or peroxidase is used as the labeling enzyme.

For example, 2', 7'-clichlorofluorescein is a fluorescence-generating substrate (or fluorescence-generating compound) capable of being used in reaction systems comprising peroxidase and hydrogen peroxide (A. S. Ferrer, et al. Anal. Biochem., 187, 129 (1990)). In that reaction system, in general, coloring substrates such as diaminobenzidine derivatives are often used because of their color stability, although their sensitivity is lower than that of fluorescence-generating substrates (for example, see P. D. Josephy, et al., J. Biol. Chem., 258, 5561 (1983); E. Sheldon, et al., Clin. Chem., 33, 1368 (1987)).

3-(p-hydroxyphenyl) propionic acid (K. Zaitsu, et al., in Anal. Biochem., 109, 109–113 (1980)), N-alkylcarbonyl-p-hydroxyanilides (Japanese Patent Publication (JP-B) Hei-7–108238) and N-aroyl-p-aminoanilides (S. Fujita, et al., in Chemistry-y Letters, 1075–1076 (1997)) have relatively simple structures, and are interesting fluorescence-generating substrates capable of reacting in a system that comprises peroxidase and hydrogen peroxide.

Use of these fluorescence-generating substrates only partially achieves the desired object. However, where hydrogen peroxide is reacted with peroxidase on a solid support in the presence of any of such substrates, and it is desired that the fluorescent dye formed by the reaction is kept on the support, a high-resolution assay is not always possible. For example, the fluorescent region will broaden because of the relatively high solubility of the dye in aqueous media.

SUMMARY OF THE INVENTION

Tile object of the present invention is to provide a novel means of using fluorescence-generating substrates, which is free from the problems of the prior art, noted above. In particular, this invention solves the shortcomings of fluorescence-generating substrates that are used on solid supports. Specifically, the object of the invention is to provide improved fluorescence-generating substrates which generate fluorescent dyes having reduced mobility on solid supports, and also to provide a method of using these substrates.

After studying the behavior of various compounds in reaction systems comprising peroxidase and hydrogen peroxide, we have found that various p-hydroxyphenyl derivatives, which have lower water solubility than that of 3-(p-hydroxyphenyl)propionic acid, noted above, can form substantially water-insoluble fluorescent dyes in the reaction system, and that the possibility of those dyes being formed on solid biological samples is extremely low.

Accordingly, to attain the object noted above, the invention provides a composition for forming fluorescent dyes in oxidative environments, which is characterized by containing a fluorescence-generating substrate (or fluorescent dye precursor) of a formula (1):

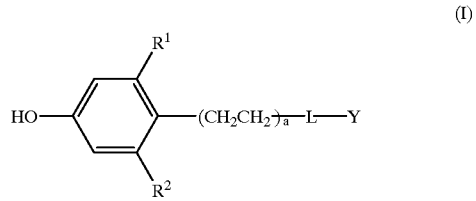

(I)

where $R^1$ and $R^2$ each independently represent a hydrogen atom, an electron-donating group selected from a lower alkyl group, a lower alkoxy group, a hydroxyl group, an alkylcarbonyloxy group, an amino group di-substituted with lower alkyl groups, or an aryl group;

L represents —NHCO— or —CONH—;

Y represents an -alkylene-COOH group, or a group of structure (II):

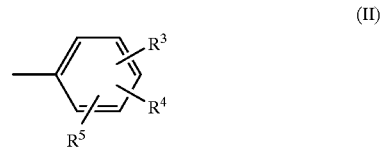

(II)

where $R^3$, $R^4$ and $R^5$ each independently represent a group as defined above for $R^1$ and $R^2$, or a carboxyl group; or two of $R^3$, $R^4$ and $R^5$ are groups that form, together with the adjacent carbon atoms to which they bond, a fused 5-membered or 6-membered hydrocarbon ring;

alkylene is defined as a linear or branched $C_{1-6}$ alkylene group; and a represents an integer of 0 or 1.

Another embodiment of the invention also provides for a method of detecting an analyte, which comprises:
preparing a biological sample that may contain an analyte to be detected,
applying a peroxidase to the sample containing hydrogen peroxide,
reacting the peroxidase enzyme with hydrogen peroxide in the presence of the fluorescence-generating substrate of formula (I) mentioned above,
and measuring the intensity of the fluorescence of the fluorescent dye thus formed, thereby detecting the presence or absence of the analyte, or measuring the concentration of the analyte.

DETAILED DESCRIPTION OF THE INVENTION

Figure 1:
FIG. 1 is a picture of the fluorescence-microscopic image of the fluorescence signal from chromosomes obtained from human peripheral blood lymphocytes (cells), using Compound 3.

The terminology "fluorescence-generating substrate" as referred to herein is meant to indicate a compound which generates a fluorescent dye, after having been oxidized in an oxidative environment; for example, after oxidation in a reaction system comprising peroxidase and hydrogen peroxide. The terminology "fluorescent dye" also referred to herein is meant to include compounds capable of generating fluorescence after absorbing radiation, as well as specific coloring dyes which do not emit light having satisfactory intensity after absorbing radiation, but which can be detected by any spectrometric means.

The lower alkyl groups, and the allkyl moiety of the lower alkoxy groups of $R^1$ and $R^2$ in formula (I), are defined as linear or branched alkyl groups having from 1 to 6 carbon atoms. Specific examples of the alkyl groups include methyl, ethyl, n-propyl, i-propyl, n-butyl, sec-butyl, tert-butyl, n-pentyl, tert-pentyl and n-hexyl groups. Methyl groups are especially preferred.

The aryl groups include, for example, phenyl, tolyl and naphthyl groups which may be substituted by any of hydroxyl, lower alkyl, lower alkoxy groups, or halogen atoms. Phenyl groups are especially preferred.

At least one of $R^1$ and $R^2$ is preferably a hydrogen atom. Where both $R^1$ and $R^2$ are not hydrogen atoms, they are preferably any of a methyl group or a methoxy group.

L is —NHCO— or —CONH—.

Y is -alkylene-COOH, where alkylene is a linear or branched $C_{1-6}$ alkylene group. Alternatively, Y is formula (II):

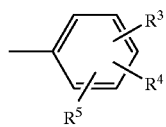

(II)

where $R^3$, $R^4$ and $R^5$ each independently represent a group as defined above for $R^1$ and $R^2$, or a carboxyl group; or two of $R^3$, $R^4$ and $R^5$ are groups that form, together with the adjacent carbon atoms to which they bond, a fused 5-membered or 6-membered hydrocarbon ring. $R^3$, $R^4$ and $R^5$ may be bonded to the carbon atoms at any position in the benzene ring, as long as the compounds of formula (I) meet the object of the invention. When $R^3$, $R^4$ and $R^5$, are bulky substituents, however, it is desirable that they be attached to the ring para to the linking group, L. Two of $R^3$, $R^4$ and $R^5$ may form, together with the adjacent carbon atoms to which they bond, a 5-membered or 6-membered hydrocarbon ring, fused to the benzene ring to which it bonds. In that case, the fused ring structure may be represented by:

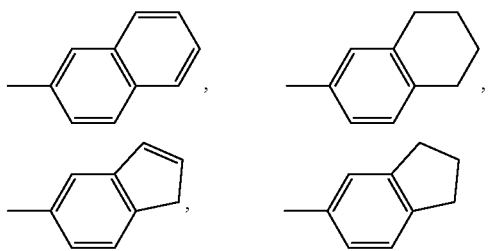

When Y is -alkylene-COOH, the alkylene group may include metlhylene, ethylene, trimethylene, propylene, tetramethylene, isopropylmethylene, pentamethylene, hexamethylene, 2-isopropyltrimethylene. Pentamethylene and hexamethylene are preferred.

Preferred examples of the combination of the moieties in formula (I) are as follow. When a is 0, it is preferable that L is —NHCO— and Y is formula (II):

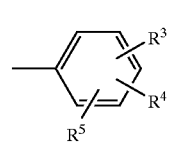

(II)

When a is 1, it is preferable that L is —CONH— and Y is alkylene-COOH.

Some of the compounds of formula (I) are known, or can be produced by known methods. Other novel compounds of formula (I) could be produced by anyone skilled in the art, for example, according to the methods described in the Production Examples.

It is presumed that the p-hydroxyplhenyl derivatives of formula (I), used in the present invention, will covalently bond with each other at the ortho-position relative to the hydroxyl group in oxidative environments, to produce dimerized or trimerized fluorescent dyes. The fluorescent dyes thus formed are, in general, barely soluble in aqueous media. In addition, they have the ability to bind to, or have an affinity for porous synthetic resins such as polyurethane or the like, on specific synthetic resin membranes such as nylon membranes, nitrocellulose membranes, polyvinylidene difluoride (PVDF) membranes or the like, on chromosomes in cell preparations, or on solid biological samples such as tissues, or the like. In particular, when the solid supports carry nucleic acids, the binding ability of the dyes is significantly enhanced.

The composition of the invention generally comprises the fluorescence-generating substrate of formula (I), along with a suitable solvent. The substrate may be incorporated into the composition in the form of a solution or suspension. If it is desired that the composition contain a solution of the substrate, the substrate can be dissolved in an aqueous medium that contains a water-miscible, organic co-solvent, such as dimethylformamide, acetonitrile or the like.

The oxidative environments referred to herein include any environment in which the fluorescence-generating substrates of formula (I) can be converted into fluorescent dyes. One preferred example is a reaction system comprising peroxidase and hydrogen peroxide. The peroxidase may be typically horseradish peroxidase.

The "solid support" to which peroxidase binds, as referred to herein, includes, for example, porous carriers of synthetic resin such as polyurethane or the like, and synthetic resin membranes of nylon, nitrocellulose, PVDF and the like, such as those mentioned above, as well as biological samples. Specifically, biological samples include animal and vegetable tissue slices, cell preparations, chromosomes, tissue cells and others as prepared for histochemical studies. The peroxidase binds to supports, Such as the abovementioned, by reacting, bonding, or complexing with nucleic acids (DNA, RNA) present on the porous carrier or a polymer membrane, or nutcleic acids present in biological samples. Optionally, the peroxidase can complex with a nucleic acid probe, a hapten or the like. For example, peroxidase may bind to an antigen or antibody on a support, in the form of an antigen-peroxidase labeled antibody or an antibody-antigen-peroxidase labeled antibody. DNA or RNA could be an antigen by itself. Peroxidase may bind to DNA or RNA on a support, for example, in the form of a DNA or RNA-(hybridized) -digoxigenin labeled DNA probe-peroxidase labeled anti-digoxigenin antibody. The symbol "-", as referred to herein, indicates an immune complex-forming bond; and "-(hybridized)-" indicates an intercomplementary hybridization bond between DNA or RNA and a DNA probe.

As mentioned above, the fluorescent dyes formed from the compounds of formula (I) used in the invention, have a high affinity for solid supports themselves, or for nucleic acids carried on solid supports. Therefore, when a compound of formula (I) is present, in a reaction system comprising hydrogen peroxide and peroxidase bonded to a solid support, the fluorescent dye is formed in situ from the compound of formula (I) by means of the intended reaction. These fluorescent dyes can bind to the support, or to the nucleic acid carried on the support. Accordingly, the composition of the present invention is advantageously used in in-situ fluorometric immunoassay. However, the invention does not exclude the use of the fluorescence-generating substrates of formula (I) in measurement of hydrogen peroxide formed, for example, from clinically important compounds of glucose, urea, amino acids or the like in the presence of glucose oxidase, uric acid oxidase, amino acid oxidase, or the like.

As mentioned above, the composition of this invention can be used for detecting specific substances in biological specimens. The biological specimens include animal fluids, such as blood, urea, etc., as well as animal and vegetable tissue slices. Saccharides, lipids, amino acids, nucleic acids, proteins and other substances that may exist in such specimens could be the analytes to be detected in the invention. In general, well known immunloassays are appropriate for the detection of those analytes. Antibodies labeled with peroxidase are suitable for detecting nucleic acids and proteins (e.g., receptors) in tissue specimens. For detecting nucleic acids, samples may be processed in a reaction system comprising peroxidase, that may not be bonded to a solid support, and hydrogen peroxide, along with a compound of formula (I), so that the fluorescent dye formed in situ is bound to the nucleic acid to be detected.

Qualitative or quantitative detection of a fluorescent dye may be attained by applying a specific wavelength of radiation to the dye, followed by measuring the fluorescence energy generated by the dye. In quantitative detection, the intensity of the fluorescence energy generated may be related to the amount of the analyte existing in the samples. The fluorescence energy may be measured with any suitable, commercially available detectors.

The invention is described in more detail with reference to the following Production Examples and Use Examples, which, however, are not intended to restrict the scope of the invention.

PRODUCTION EXAMPLE 1

Production of 4-hydroxy-2-methylphenyl-2,5-dimetlhoxybenzamide

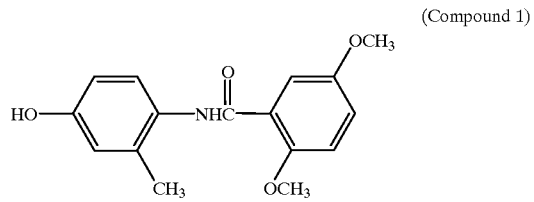

(Compound 1)

(1) Production of 2,5-dimethoxybenzoyl chloride:

2,5-dimethoxybenzoic acid (643 mg, 3.53 mmols) was put into a 30-ml two-neck flask, purged with argon, and dissolved in 1 ml of dry methylene chloride. Next, thionyl chloride (0.5 ml, 7.05 mmols) was added to the flask, and heated under reflux at 70° C. for 5 hours. Next, the solvent was removed by evaporation under reduced pressure, using an aspirator.

(2) Production of 4-hydroxy-2-mnetlhylphenyl-2,5-dimethoxybenzamide:

4-Amino-3-metlhylphenol (304 mg, 2.47 mmols) was put into a 30-ml conical flask, purged with argon, and dissolved in 10 ml of dry dimethylformamide (DMF). Next, a DMF solution (2 ml) of 2,5-dimethoxybenzoyl chloride (708 mg, 3.53 mmols) was added, and stirred at room temperature for 12 hours. The resulting reaction mixture was poured into 75 ml of cold water, suction-filtered, extracted with methylene chloride, and washed with water. The methylene chloride layer was dried with sodium sulfate, and the methylene chloride was removed by evaporation under reduced pressure. Next, the residue was purified by column chromatography (silica gel eluted with methylene chloride) to obtain 302 mg of the intended product, 4-hydroxy-2-methylphenyl-2,5-dimethoxybenzamide (yield: 43%).

$^1$H-NMR (200 MHz, DMSO-d$_6$), δ: 2.21 (3H, s) 3.76 (3H, s), 3.93 (3H, s), 6.59 (1H dd, J=2.7 and 8.5), 6.65 (1H, d, J=2.5), 7.08 (1H, dd, J=3.0 and 9.0), 7.15 (1H, d, J=9.0), 7.44 (1H, d, J=2.7), 7.57(1H, d, J=8.5), 9.17 (1H, s), 9.63 (1H, s).

PRODUCTION EXAMPLE 2

Production of 4-hydroxy-2-methylphenyl-4-pheenylbenzamide

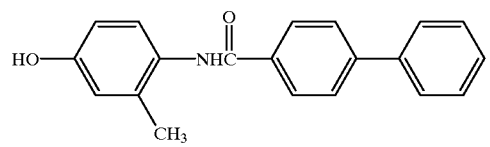

(Compound 2)

4-Amino-3-methylphenol (270 mg, 2.20 mmols) was put into a 30-ml conical flask, purged with argon, and dissolved in 1.0 ml of dry DMF. Next, 0.3 ml (1 eq.) of dry triethylamine was added. Next, a dry DMF solution (3.0 ml) of 4-phenylbenzoyl chloride (478 mg) was added, and stirred at room temperature for 12 hours. The resulting reaction mixture was poured into 100 ml of cold water, suction filtered, extracted with methylene chloride, and washed with water. The methylene chloride layer was dried with sodium sulfate, and methylene chloride was removed by evaporation under reduced pressure. Next, the residue was purified by column chromatography (silica gel eluted with methylene chloride) to obtain 648 mg of the intended product, 4-hydroxy-2-methylphenyl-4-phenylbenzamide (yield: 96%).

$^1$H-NMR (200 MHz, DMSO-d$_6$), δ: 2.14 (3H, s), 6.61 (1H, dd, J=2.7 and 8.4), 6.68 (1H, d, J=2.5), 7.08 (1H, d, J=8.4), 7.38 to 7.55 (3H, m), 7.73 to 7.83 (4H, m), 8.60 (2H, d, J=8.2), 9.28 (1H, s), 9.72 (1H, s).

PRODUCTION EXAMPLE 3

Production of 4-hydroxy-2-methylphenylbenzamide (Compound 3)

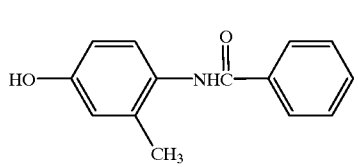

4-Amino-3-methylphenol (370 mg, 3.00 mmols) was put into a 30-ml conical flask, purged with argon, and dissolved in 1.3 ml of dry DMF. Next, 0.42 ml (1 eq.) of dry triethylamine was added. Then, a dry DMF solution (3.0 ml) of benzoyl chloride (0.35 ml) was added, and stirred at room temperature for 12 hours. The resulting reaction mixture was poured into 50 ml of cold water, suction filtered, extracted with methylene chloride, and washed with water. The methylene chloride layer was dried with sodium sulfate, and methylene chloride was removed by evaporation under reduced pressure. Next, the residue was purified by column clromnatography (silica gel eluted with methylene chloride) to obtain 400 mg of the intended product, 4-hydroxy-2-methylphenylbenzamide (yield: 60%).

$^1$H-NMR (200 MHz, DMSO-d$_6$), δ: 2.13 (3H, s), 6. 60 (1H, dd, J=2.7 and 8.5), 6.66 (1H, d, J=2.7), 7.05 (1H, d, J=8.5), 7.45 to 7.60 (3H, m), 7.95 (2H, d, J=7.1), 9.25 (1H, s), 9.65 (1H, s).

PRODUCTION EXAMPLE 4

Production of 4-hydroxypheniylbenzamide (Compound 4)

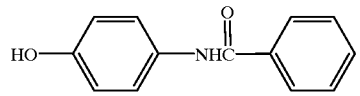

4-Aminophaeniol (328 mg, 3.00 mmols) was put into a 30-ml conical flask, purged with argon, and dissolved in 1.3 ml of dry DMF. Then, 0.42 ml (1 eq.) of dry triethylamine was added. Next, a dry DMF solution (3.0 ml) of benzoyl chloride (0.35 ml) was added , and stirred at room temperature for 12 hours. The resulting reaction mixture was poured into 50 ml of cold water, suction filtered, extracted with methylene chloride, and washed with water. The methylene chloride layer was dried with sodium sulfate, and methylene chloride was removed by evaporation under reduced pressure. Next, the residue was purified by column chromatography (silica gel eluted with methylene chloride) to obtain 330 mg of the intended product, 4-hydroxyphenylbenzamide (yield: 51.6%).

$^1$H-NMR (200 MHz, DMSO-d$_6$), δ: 6.72 (1H, dd, J=2.2 and 9.1), 7.45 to 7.56 (5H, m), 7.92 (2H, d, J=2.2 and 7.8), 9.19(1H, s), 9.98 (1H, s).

PRODUCTION EXAMPLE 5

Production of 4-hydroxyphenyl-2-naphthoylamide (Compound 5)

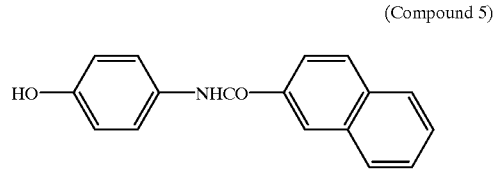

2-Naphthoyl chloride was added to a DMF solution of a mixture of 4-aminophenol and triethylamine, and stirred at room temperature for 1.5 hours. The relative amount of each compound used, and the purification of the product, is described in Production Example 4. Thus was obtained the intended product, 4-hydroxyphenyl-2-naphthoylamide (yield: 33%)

$^1$H-NMR (200 MHz, DMSO-d$_6$), δ: 6.75 (1H, dd, J=2.2 and 9.1), 7.55 to 7. 65 (3H, m), 7.96 to 8.07 (4H, m), 8.53 (d, J=2.2 and 7.8). 9.21 (1H, s), 10.17 (1H, s).

PRODUCTION EXAMPLE 6

Production of 4-hydroxyphenyl-1-naphthoylamide (Compound 6)

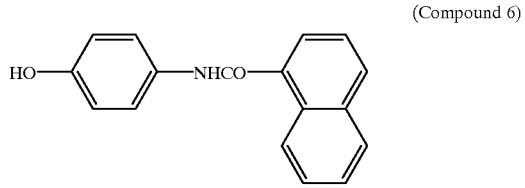

1-Naphthoyl chloride was added to a DMF solution of a mixture of 4-aminophenol and triethylamine, and stirred at room temperature for 1 hour. The relative amount of each compound used, and the purification of the product, is described in Production Example 4. Thus was obtained the intended product, 4-hydroxyphenyl-1-naphthoylamide (yield: 28%).

$^1$H-NMR (200 MHz, DMSO-d$_6$), δ: 6.72 (1H, dd, J=2.2 and 9.1), 7.54 to 7.71 (6H, M), 7.96 to 8.21 (3H, m), 9.15 (1H, s), 10.24 (1H, s).

PRODUCTION EXAMPLE 7

Production of 4-hydroxy-2-methylphenyl-4-methylbenzamide (Compound 7)

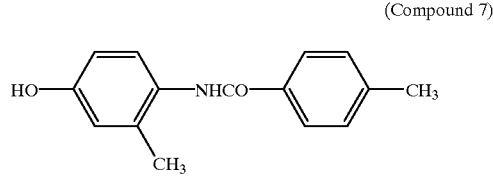

4-Methylbenzoyl chloride was added to a DMF solution of a mixture of 4-amino-3-methylphenol and triethylamine, and stirred at room temperature for 30 minutes. The relative amount of each compound used, and the purification of the product. is described in Production Example 4. Thus was obtained the intended product, 4-hydroxy-2-methylphenyl-4-methylbenzamide (yield: 12%).

$^1$H-NMR (200 MHz, DMSO-$d_6$), δ: 2.11 (3H, s), 2.37 (3H, s), 6.55 to 6.65 (2H, m), 7.02 (1H, d, J=9.1), 7.29 (1H, d, J=9.1), 7.85 (1H, d, J=9.1), 9.24 (1H, s), 9.57 (1H, s).

PRODUCTION EXAMPLE 8

Production of 4-hydroxy-2-methylphenyl-4-methoxybenzamide (Compound 8)

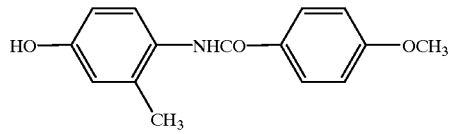

4-Methoxybenzoyl chloride was added to a DMF solution of a mixture of 4-amino-3-methylphenol and triethylamine, and stirred at room temperature for 5 minutes. The relative amount of each compound used, and the purification of the product, is described in Production Example 4. Thus was obtained the intended product, 4-hydroxy-2-methlylplhellyl-4-methoxybenzamide (yield: 16%).

$^1$H-NMR (200 MHz, DMSO-$d_6$), δ: 2.11 (3H, s), 3.83 (3H, s), 6.55 to 6.65 (2H, m), 7.02 (1H, dd, J=2.2 and 9.1), 7.93 (1H, dd, J 2.2 and 9.1), 9.23 (1H, s), 9.5 (1H, s).

PRODUCTION EXAMPLE 9

Production of 4-hydroxy-2-methylphenyl1–2-methoxybenzamide (Compound 9)

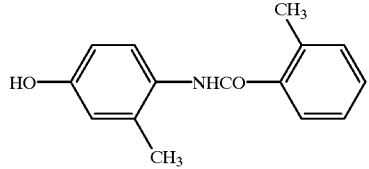

The Compound 9 was obtained in the same manner as in Production Example 3, except that 2-methylbenzoyl chloride was used in place of the benzoyl chloride used in Production Example 3.

$^1$H-NMR (200 MHz, DMSO-$d_6$), δ: 2.17 (3H, s), 2.41 (3H, s), 6.58, (1H, dd, J=8.3, 2.5), 6.64 (1H, d, J=2.5), 7.09 (1H, d, J=8.3), 7.22–7.40 (3H, m), 7.47 (1H, dd, J=7.2, 2.2), 9.24 (1H, s), 9.48 (1H, s).

PRODUCTION EXAMPLE 10

Production of 4-hydroxy-2-methylphenyl-2,4,6-trimethylbenzamide (Compound 10)

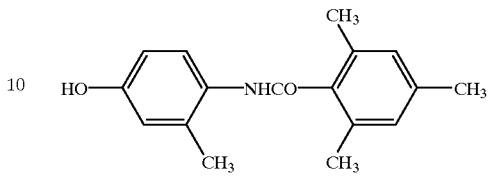

The Compound 10 was obtained in the same manner as in Production Example 3, except that 2,4,6-trimethylbenzoyl chloride was used in place of the benzoyl chloride used in Production Example 3.

$^1$H-NMR (200 MHz, DMSO-$d_6$), δ: 2.25 (3H, s), 2.31 (3H, s), 2.42 (6H, s), 5.40 (1H, s), 6.67 (1H, d, J=6.5 HZ), 6.70 (1H, s), 6.91 (2H, s), 6.99 (1H, s), 7.54 (1H, d, J=6.6).

PRODUCTION EXAMPLE 11

Production of 6-{3-(4-hydroxyphenyl)propionamido}hexanoic acid (Compound 11)

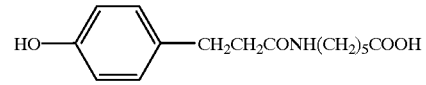

(1) Benzyloxycarbonyl Protection of Hydroxyl Group in 3-(4-hydroxyphenyl)propionic Acid:

3-(4-Hydroxyphenyl)propionic acid (200 mg, 1.2 mmols) was put into a 50-ml conical flask, and dissolved in a mixed solvent of 2.4 ml of aqueous 2 N sodium hydroxide and 2.4 ml of tetrahydrofuran. Benzyloxycarbonyl chloride (0.34 ml, 2.4 mmols) was added, and stirred at room temperature for 2 hours. The reaction was terminated by the addition of 1 N hydrochloric acid. The reaction mixture was then extracted with methylene chloride, and purified by a column chromatography. The yield of the product was 77%. The structure of the product was identified by $^1$H-NMR.

$^1$H-NMR (200 MHz, CDCl$_3$), δ: 2.67 (2H, t, J 7.0), 2.96 (2H, t, J=7.0), 5.26 (2H, s) 7.10 (2H, d, J 8.5), 7.22 (211, d, J=8.6).

(2) Succinimidyl Esterification of the Benzyloxycarbonyl (Cbz)-protected Compound Prepared in (1):

The Cbz-protected 3-(4-hydroxyphenyl)propionic acid (100 mg, 0–33 mmols) was put into a 30-ml conical flask, and purged with argon. The compound was cooled to 0° C., and completely dissolved in 2 ml of dry methylene chloride. To this was added N-hydroxysuccinimide (41.8 mg, 0.36 mmols) dissolved in dry methylene chloride and dry acetonitrile (2.2 ml). Next, N,N-dicyclohexylcarbodiimide (81.7 mg, 0.4 mmols) dissolved in dry methylene chloride (0.41 ml) was added to the flask, and stirred for 2 hours at room temperature. The absence of the starting compound in the reaction mixture was confirmed by TLC. The reaction mixture was then suction filtered to remove the precipitate, and the solvent was removed by evaporation under reduced pressure. Because the compound thus produced decomposed extremely easily, it was used without isolation in the next step.

(3) Production of Cbz-protected 6-{3-(4-hydroxyphenyl)propionamido}hexane:

6-Aminohexanoic acid (130 mg, 0.99 mmols) was put into a 30-ml conical flask, and dissolved in pH 9.0 buffer. The compound prepared in previous step 2 (81.7 mg), dissolved in tetrahydrofuran, was immediately added, at room temperature. After continuing for 2 hours at room temperature, the reaction was terminated by addition of aqueous 4 N hydrochloric acid. The reaction mixture was extracted with ethyl acetate, and then purified by column chromatography to obtain 103 mg of the intended product (yield: 76%). The structure of the compound was identified by $^1$H-NMR.

$^1$H-NMR (200 MHz, CDCl$_3$), δ: 1.30 (2H, t, J=7.7), 1.44 (2H, t, J=7.7), 1.61 (2H, t, J=7.6), 2.95 (2H, t, J=7.4), 3.20 (2H, t, J=6.4), 5.26 (2H, s), 5.5 (1H, brs), 7.07 (2H, d, J=8.6), 7.21 (2H, d, J=8.5).

(4) Production of 6-{3-(4-hydroxyphenyl)propionamido}hexanoic acid:

The Cbz-protected 4-hydroxyphenylethyleneamidohexanoic acid (103 mg, 0.25 mmols) and palladium hydroxide on carbon (35 mg) were added to a 30-ml conical flask, and dissolved in 3 ml of dry ethanol. Next, hydrogen gas was introduced, and the reaction was continued for 8 hours at room temperature under a hydrogen atmosphere. The absence of the starting compound in the reaction mixture was identified by TLC, and the reaction mixture was suction filtered. The resulting residue was dried under vacuum to obtain 69 mg of the intended product (yield: 98%). The structure of the compound was identified by $^1$H-NMR.

$^1$H-NMR (200 MHz, DMSO-d$_6$), δ: 1.21–1.52 (6H, m), 2.17 (2H, t, J=7.4), 2.25 (2H, t, J=7.4), 2.65 (2H, t, J=8.5), 2.99 (2H, q, J=5.8), 6.62 (2H, d, J 8.5), 6.95 (2H, d, J=8.5), 7.60 7.78 (1H, brs), 8.83 9.20 (1H, brs), 11.79–12.10 (1H, brs).

Use Example: In-situ Hybridization of a Human Chromosome:

A human chromosome sample was hybridized with a digoxigenin-labeled, full-length human DNA probe, to which was bonded a peroxidase-labeled anti-digoxigenin antibody. This was reacted with any of fluorescence-generating substrates of the invention (Compounds 1 to 11) or with a comparative substrate of a commercially available, water-soluble fluorescent substrate, 3-(4-hydroxyphenyl)propionic acid (HPPA). The resulting fluorescence emitted in each system was observed with a fluorescence microscope. The full-length human DNA probe hybridizes entirely with the human chromosome. Therefore, if the fluorescence-generating substrates tested herein are reacted in a reaction system comprising peroxidase and hydrogen peroxide, the entire chromosome in the system shall be seen to emit fluorescence in the fluorescence-microscopic observation.

The procedure is as follows:

Human chromosome samples were prepared from cultured human peripheral blood lymphocytes. Full-length human DNA was labeled with digoxigenin through nick translation, collected through ethanol precipitation, and dissolved in formamide to prepare a digoxigenin-labeled, full-length human DNA probe. Each human chromosome sample was immersed in a denaturing solution kept heated at 70° C., for 2 minutes, and then rapidly cooled by putting it into 70% ethanol cooled to 4° C., whereby the double-stranded DNA of the sample was kept dissociated in a single-stranded condition. The probe was kept in a water bath at 75° C. for 10 minutes, and then rapidly cooled in ice water with 5 minutes, whereby the double-stranded DNA of the probe was kept dissociated in a single-stranded condition. This probe was mixed with a hybridization solution, put on the human chromosome sample, and reacted with it overnight at 37° C. (in-situ hybridization).

After having been hybridized, the system was washed with a solution of 50% formamide/2×SSC at 37° C. for 15 minutes, then with 2×SSC at room temperature for 15 minutes, and then with 4×SSC at room temperature for 5 minutes, thereby removing the excess, non-hybridized probe therefrom. Next, a peroxidase-labeled anti-digoxigenin antibody was diluted with a 1% blocking solution into a 1/100 dilution, and the resulting enzyme-labeled antibody dilution was put on the sample, and maintained at 37° C. for 1 hour. The excess enzyme antibody not bonded to the probe was removed by washing the system with a washing solution containing a surfactant. Any of the fluorescence-generating substrates (Compounds 1 to 11) of the invention and a commercially-available, water-soluble fluorescent substrate, HPPA was dissolved in a reactant solution containing 0.01% hydrogen peroxide (1 mM), and the resulting fluorescent substrate solution was put on the sample and reacted with it at room temperature for 30 minutes. After reacting in the reaction system comprising the probe-bonded peroxidase and hydrogen peroxide, the fluorescence-generating substrate formed a new compound which was fixed on the chromosome and emitted fluorescence, which was observed using a fluorescence microscopic.

The full-length human DNA probe hybridizes with the entire chromosome, with the result that the entire chromosome was stained with the fluorescence-generating substrate. Sample were processed with any of the fluorescent substrates (Compounds 1 to 11) as well as the commercially-available, water-soluble fluorescent substrate, LIPPA. The fluorescence of the samples was observed with a fluorescence microscope, and the intensity of fluorescence from the sample was measured. In addition, the binding of the substrate to the chromosome was checked.

The test results are shown in Table 1. The criteria for evaluation are as follows:

| | |
|---|---|
| +++: | Very strong. |
| ++: | Strong. |
| +: | Weak. |
| ±: | Very weak. |
| −: | Not detected. |

TABLE 1

Characteristics of Fluorescence-Generating Substrates in In-situ Chromosome Hybridization

| | Observation | | |
|---|---|---|---|
| | Intensity of Fluorescence | Binding | Color of Fluorescence |
| Comparison (HPPA) | ± | + | green |
| Compound 1 | ++ | ++ | green |
| Compound 2 | + | ++ | green |
| Compound 3 | ++ | ++ | green |
| Compound 4 | + | ++ | green |
| Compound 5 | ++ | ++* | green |
| Compound 6 | + | ++ | green |
| Compound 7 | ++ | ++ | green |
| Compound 8 | ++ | ++ | green |
| Compound 9 | ++ | ++ | green |

TABLE 1-continued

Characteristics of Fluorescence-Generating
Substrates in In-situ Chromosome Hybridization

| | Observation | | |
|---|---|---|---|
| | Intensity of Fluorescence | Binding | Color of Fluorescence |
| Compound 10 | ++ | ++ | green |
| Compound 11 | +++ | +++ | green |

*with much noise.

The product from HPPA after the enzymatic reaction was soluble in water or could not bind to the chromosome. In the system using HPPA, therefore, few fluorescent signals were detected. In contrast, all of the products of the fluorescence-generating substrates of the invention gave high-intensity fluorescence and had high binding to the chromosome. In particular, in samples prepared with Compounds 3, 7, 8 and 11, high-intensity fluorescent signals were observed.

FIG. 1 is a fluorescence-microscopic image of the fluorescence signal from a sample prepared with Compound 3, showing a g,reen-stained chromosome site (the white area in the upper portion of the picture). Since the fluorescent substrates of the invention can bind not only to chromosomes, but also to tissues, they can be used for immunostaining tissues.

While the invention has been described in detail and with reference to specific embodiments thereof, it will be apparent to one skilled in the art that various changes and modifications can be made therein without departing from the spirit and scope thereof.

Japanese patent applications 10-73094 filed Mar. 9, 1998 and 10-376986 filed Dec. 28, 1998 are incorporated herein by reference.

What is claimed is:

1. A composition for forming fluorescent dyes in oxidative environments, which comprises a fluorescence-generating substrate or fluorescent dye precursor of formula (I):

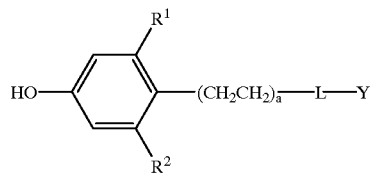

(I)

wherein $R^1$ and $R^2$ are each independently selected from the group consisting of a hydrogen atom, or an electron-donating substituent;
  wherein the electron-donating substituent is selected from the group consisting of a lower alkyl group, a lower alkoxy group, a hydroxyl group, an alkylcarbonyloxy group, an amino group di-substituted with a lower alkyl group, or an aryl group;
  and, wherein L is selected from the group consisting of —NHCO— and, —CONH—;
  and wherein Y is selected from the group consisting of -alkylene-COOH and formula (II):

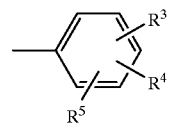

(II)

wherein $R^3$, $R^4$ and $R^5$ are each independently selected from the group consisting of a hydrogen atom, a carboxyl group, a 5- or 6-membered hydrocarbon ring fused to the aromatic ring formed by any two of $R^3$, $R^4$ and $R^5$, together with the adjacent carbon atoms to which they bond, and an electron-donating substituent;
  wherein the electron-donating substituent is selected from the group consisting of a lower alkyl group, a lower alkoxy group, a hydroxyl group, an alkylcarbonyloxy group, an amino group di-substituted with a lower alkyl group, and an aryl group;
  and, wherein, -alkylene- is selected from the group of linear and branched $C_{1-6}$ alkylene groups;
  and, wherein a is 1.

2. The composition of claim 1, wherein L, is —NHCO—; Y is formula (II):

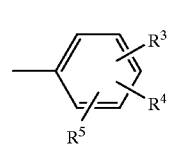

(II)

wherein $R^3$, $R^4$ and $R^5$ are each independently selected from the group consisting of a hydrogen atom, a carboxyl group, a 5- or 6-membered hydrocarbon ring fused to the aromatic ring formed by any two of $R^3$, $R^4$ and $R^5$, together with the adjacent carbon atoms to which they bond, and an electron-donating substituent;
  wherein the electron-donating substituent is selected from the group consisting of a lower alkyl group, a lower alkoxy group, a hydroxyl group, an alkylcarbonyloxy group, an amino group di-substituted with a lower alkyl group, and an aryl group;
  and a is 0.

3. The composition of claim 1, wherein L is —NHCO—; Y is -alkylene-COOH, wherein, -alkylene- is selected from the group of linear and branched $C_{1-6}$ alkylene groups;
  and a is 1.

4. The composition of claim 1, wherein the oxidative-environment is a reaction system comprising peroxidase and hydrogen peroxide.

5. The composition of claim 2, wherein the oxidative-environment is a reaction system comprising peroxidase and hydrogen peroxide.

6. The composition of claim 3, wherein the oxidative-environment is a reaction system comprising peroxidase and hydrogen peroxide.

7. The composition of claim 4, wherein the oxidative environment is a reaction system comprising peroxidase bonded to a solid support, and hydrogen peroxide.

8. The composition of claim 5, wherein the oxidative environment is a reaction system comprising peroxidase bonded to a solid support, and hydrogen peroxide.

9. The composition of claim 6, wherein the oxidative environment is a reaction system comprising peroxidase bonded to a solid support, and hydrogen peroxide.

10. The composition of claim 7, wherein the solid support is a biological sample, and peroxidase is bonded to said biological sample via immune complex formation.

11. The composition of claim 8, wherein the solid support is a biological sample, and peroxidase is bonded to said biological sample via immune complex formation.

12. The composition of claim 9, wherein the solid support is a biological sample, and peroxidase is bonded to said biological sample via immune complex formation.

13. The composition of claim 10, wherein the biological sample is a chromosome, cell or body tissue sample.

14. The composition of claim 11, wherein the biological sample is a chromosome, cell or body tissue sample.

15. The composition of claim 12, wherein the biological sample is a chromosome, cell or body tissue sample.

16. The composition of claim 7, wherein the solid support is a porous carrier or polymer membrane having a nucleic acid fixed thereon, and peroxidase is bonded to said support via immune complex formation with the nucleic acid, or via hybridization with a nucleic acid probe and said nucleic acid.

17. The composition of claim 8, wherein the solid support is a porous carrier or polymer membrane having a nucleic acid fixed thereon, and peroxidase is bonded to said support via immune complex formation with the nucleic acid, or via hybridization with a nucleic acid probe and said nucleic acid.

18. The composition of claim 9, wherein the solid support is a porous carrier or polymer membrane having a nucleic acid fixed thereon, and peroxidase is bonded to said support via immune complex formation with the nucleic acid, or via hybridization with a nucleic acid probe and said nucleic acid.

19. A method for detecting and measuring the concentration of an analyte, which comprises the steps of preparing a biological sample that may contain the analyte to be detected, applying a peroxidase to said biological sample in the presence of hydrogen peroxide, reacting said peroxidase with hydrogen peroxide in the presence of a fluorescence-generating substrate of claim 1, and measuring the intensity of the fluorescence of the fluorescent dye thus formed.

20. The method of claim 19, wherein the peroxidase is bonded to a solid biological sample through formation of an immune complex.

21. The method of claim 19, wherein the analyte to be detected in the sample is a nucleic acid, and the peroxidase is bonded to the sample via immune complex formation with the nucleic acid or via hybridization with a nucleic acid probe and the nucleic acid in said sample.

22. A composition for forming fluorescent dyes in oxidative environments, which comprises a fluorescence-generating substrate or fluorescent dye precursor of formula (I):

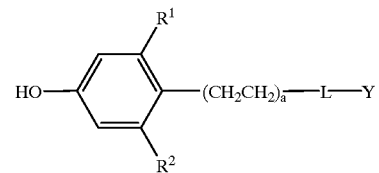

(I)

wherein $R^1$ and $R^2$ are each independently selected from the group consisting of a hydrogen atom, or an electron-donating substituent;

wherein the electron-donating substituent is selected from the group consisting of a lower alkyl group, a lower alkoxy group, a hydroxyl group, an alkylcarbonyloxy group, an amino group di-substituted with a lower alkyl group, or an aryl group;

and, wherein L is selected from the group consisting of —NHCO— and,—CONH—, and wherein Y is formula (II):

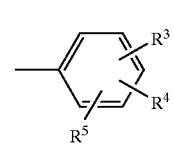

(II)

wherein $R^3$, $R^4$ and $R^5$ are each independently selected from the group consisting of a hydrogen atom, a carboxyl group, a 5- or 6-membered hydrocarbon ring fused to the aromatic ring formed by any two of $R^3$, $R^4$ and $R^5$, together with the adjacent carbon atoms to which they bond, and an electron-donating substituent;

wherein the electron-donating substituent is selected from the group consisting of a lower alkyl group, a lower alkoxy group, a hydroxyl group, an alkylcarbonyloxy group, an amino group di-substituted with a lower alkyl group, and an aryl group and, wherein a is selected from 0 or 1, and when a is 0, no more than one of $R^3$, $R^4$ and $R^5$ is a hydrogen atom.

* * * * *